United States Patent [19]
Kim et al.

[11] Patent Number: 5,866,688
[45] Date of Patent: Feb. 2, 1999

[54] PRODUCTION OF ANTI-PEPTIDE ANTIBODIES AGAINST CYTOCHROME P450

[75] Inventors: Hyesook Kim, Bloomfield Hills, Mich.; Jonathan Charnecki, Gainsville, Fla.; David A. Putt, Romeo; Edward Y. Kim, Bloomfield Hills, both of Mich.

[73] Assignee: Oxford Biomedical Research, Inc., Oxford, Mich.

[21] Appl. No.: 471,286

[22] Filed: Jun. 6, 1995

[51] Int. Cl.$^6$ .................................................. C07K 16/00
[52] U.S. Cl. ..................................... 530/357.9; 530/387.1
[58] Field of Search .............................. 530/387.1, 381.9

[56] References Cited

PUBLICATIONS

Oench et al. Anch. Biochem. Biophys. 270:23–32, 1989.
CRC Handbook of Biochem & Biophys, 3$^{rd}$ ed. vol. II, G. Fasman (ed), p. 84, 1976.
Friedman et al. Toxicologic Pathol. 12:155–61, 1984.
Letwe–Gonyon et al. vol. 119 No. 2 1984 pp. 744–750.
Bradford, "A rapid and sensitive method for quantitation of microgram quantities of protein utilizing the principle of protein–dye binding" *Anal. Biochem.*, 72:248–254 (1976).
Burke and Mayer, "Ethoxyresorufin: direct fluorimetric assay of microsomal o–dealkylation which is preferentially inducible . . . " *Drug Metabl. Dispos.*, 2(6):583–588 (1974).
Chou and Fasman, "Prediction of protein conformation" *Biochemistry*, 13(2):222–244 (1974).
Edwards et al., "An anti–peptide antibody targeted to a specific region of rat cytochrome P–450IA2 inhibits enzyme activity" *Biochem. J.*, 266:497–504 (1990).
Edwards et al., "Antipeptide antibodies in studies of cytochromes P451IA" in *Methods in Enzymol.*, 206:220–233 (Academic Press, NY) (1991a).
Edwards et al., "Identification of a functionally conserved surface region of rat cytochromes P450IA" *Biochem. J.* (Sep.), 280:749–757 (1991b).
Frey et al., "The structure of phenonbarbital–inducible rat liver cytochrome P–450 isoenzyme PB–4, Production and characterization . . . " *J. Biol. Chem.*, 260:15253–15265 (1985).
Friedberg et al., "Production of site–specific P450 antibodies using recombinant fusion proteins as antigents" in *Methods in Enzymol.*, 209:193–201 (Academic Press, NY) (1991).
Gotoh, "Substrate recognition sites in cytochrome P450 family 2 (CYP2) proteins inferred from comparative analyses . . . " *J. Biol. Chem.*, 267:83–89 (1992).
Guengerich et al., "Purification and characterization of liver microsomal cytochromes P–450: electrophoretic, . . . " Biochemistry, 21:6019–6030 (1982).
Kaul and Novak, "Inhibition and induction of rabbit liver microsomal cytochrome P–450 by pyridine" *J. Pharmacol. Exp. Ther.*, 243:384–390 (1987).
Kawajiri et al., "Coding nucleotide sequence of 3–methylcholanthrene inducible cytochrome P–450d cDNA from rat liver" *Proc. Natl. Acad. Sci., U.S.A.*, 81:1649–1653 (1984).

Kim et al., "Evidence for elevation of cytochrome P4502E1 (alcohol–inducible form) mRNA levels in rat kidney . . . " *Biochem. Biophys. Res. Commun.*, 186:846–853 (1992).
Kim et al., "Enhanced expression of rat hepatic CYP2B1/2B2 and 2E1 by pyridine: differential induction . . . " *Journal of Pharmacology and Exper. Therapeutics*, 267:927–936 (1993).
Kyte and Doolittle, "Simple method for displaying hydorpathic character of a protein" *J. Mol. Biol.*, 157:105–132 (1982).
Laemmli, "Cleavage of structural proteins during the assembly of head of bacteriophage T4" *Nature* (Aug.), 227:680–685 (1970).
Lubet et al., "Dealkylation of pentoxyresorufin: a rapid and sensitive assay for measuring induction of cytochromes(s) . . . " *Archiv. Biochem. Biophys.* (Apr.), 238(1):43–48 (1985).
Mizukami et al., "Gene structure of phenobarbital–inducible cytochrome P–450 in rat liver" *Proc. Natl. Acad. Sci. U.S.A.*, 80:3958–3962 (1983).
Murray et al., "Human hepatic CYP1A1 and CYP1A2 content, determined with specific anti–peptide antibodies . . . " *Carcinogenesis*, 14:585–592 (1993).
Nelson et al., "The P450 superfamily: update on new sequences, gene mapping, accession numbers . . . " *DNA and Cell Biol.*, 12(1):1–51 (1993).
Oda et al. "Metabolism of lidocaine by purified rat liver microsomal cytochrome P–450 isozymes" *Biochem. Pharmacol.*, 38:4439–4444 (1989).
Omura and Sato, "Carbon monoxide–binding pigment of liver microsomes" *J. Biol. Chem.*, 239:2379–2385 (1964).
Posnett et al., "A novel method for producing anti–peptide antibodies" *J. Biol. Chem.*, 263(4):1719–1725 (1988).
Poulos, "Modeling of mammalian P450s on basis of P450cam X–ray structure" in *Methods in Enzymol.*, 206:11–30 (Academic Press). (1991).
Poulos et al., "The 2.6–angstrom crystal structure of *Pseudomonas putida* cytochrome P–450" *J. Biol. Chem.*, 260:16122–16130 (1985).
Poulos et al., "Crystal structure of substrate–free *pseudomonas putida* cytochrome P–450" *Biochemistry*, 25:5314–5322 (1986).

(List continued on next page.)

*Primary Examiner*—Sheela Huff
*Attorney, Agent, or Firm*—Kohn & Associates

[57] ABSTRACT

A method for production of a form-specific and/or inhibitory antibody against a cytochrome P450 protein is disclosed. The method includes the steps of selecting a cytochrome P450 protein for which a form-specific and/or inhibitory antibody is needed. The amino acid sequence of the selected cytochrome P450 protein is determined and aligned with a comparison amino acid sequence using an alignment algorithm. A peptide sequence corresponding to a region of a substrate recognition site is identified and a peptide of the selected sequence prepared. Using the peptide as an immunogen, an inhibitory and/or form-specific antibody is produced.

24 Claims, 6 Drawing Sheets

OTHER PUBLICATIONS

Reik et al., "A simple, non–chromatographic purification procedure for monoclonal antibodies" *J. Immunol. Methods*, 100:123–130 (1987).

Sesardic et al., "Inter–relatedness of some isoenymes of cytochrome P–450 from rat, rabbit and human . . . " *Biochem. J.*, 236:569–577 (1986).

Symposium: Antibody–based therapeutics for cancer and autoimmune disease, *FASEB Meeting*, Apr. 5–9, 1992, Anaheim, CA.

Tam, "Synthetic peptide vaccine design: synthesis and properties of a high–density multiple antigenic peptide system" *Proc. Natl. Acad. Sci. U.S.A.*, 85:5409–5413 (1988).

Unger et al., "Nucleotide sequence of the *Pseudomonas putida* cytochrome P–450cam gene and its expression in *Escherichia coli*" *J. Biol. Chem.*, 261:1158–1163 (1986).

Waxman and Walsh, "Phenobarbital–induced rat liver cytochrome P–450: purification and characterization of two closely related . . . " *J. Biol. Chem.*, 257:10446–10457 (1982).

Waxman et al., "Regioselectivity and stereoselectivity of androgen hydroxylations catalyzed by cytochrome . . . " *J. Biol. Chem.*, 258:11937–11947 (1983).

Yabusaki et al., "Nucleotide sequence of a full–length cDNA coding for 3–methylcholanthrene–induced rat liver . . . " *Nucleic Acids Res.*, 12:2929–2938 (1984).

Yuan et al., "Identification and localization of amino acid substitutions between two pheonobarbital . . . " *Proc. Natl. Acad. Sci. USA*, 80:1169–1173 (1983).

Guengerich, "Oxidation of toxic and carcinogenic chemicals by human cytochrome P–450 enzymes" *Chemical Research in Toxicology*, vol. 4, No. 4, pp. 391–407 (1991).

Murray and Reidy, "Selectivity in the inhibition of mammalian cytochromes P–450 by chemical agents" *Pharmacological Reviews*, vol. 42, No. 2, pp. 85–99 (1990).

Sesardic et al., "A form of cytochrom P450 in man, orthologous to form d in the rat . . . " *Br. J. Clin. Pharmac.*, 26:363–372 (1988).

Symposium: *10th Intl. on Microsomes and Drug Oxidations*, Toronto, Canada, Jul. 18–21, 1994 (Abstract) Kim et al. "Production and characterization of inhibitory . . . ".

```
                    363                        374
A      2B1    v  P  I  G  v  P  H  R  V  T  K  D
              |  |  |  |  |  |  |  |  |  |  |  |
       2B2    a  P  I  G  l  P  H  R  V  T  K  D
```

```
AMINO ACID                    HYDROPHOBICITY
RESIDUE NO.

|           |       |     | α-HELIX K | β-SHEET 3 | β-SHEET 4 | β-SHEET 3 |
|-----------|-------|-----|-----------|-----------|-----------|-----------|
| P. PUTIDA | 101A1 |     | rperipaAceellrRFS-LVadGrilltsdyefhgvqlkkgdqillpqmLS------ |
| Rat | 2B1 | 344 | sKMPYTDAVIHEIQRFSDLVPIGvPHPVTKDTMFRGYLLPKNTEVYPILSSALHDPQYFDH |
| Rat | 2B2 | 344 | tKMPYTDAVIHEIQRFaDLaPIGIPHRVTKDTMFRGYLLPKNTEVYPILSSALHDPQYFDH |
| Rat | 1A2 | 360 | PQLPYLEAFILEIyRytSFVPFTIPHSTTRDTSLNGFhIPKecCiFiNQWQVNHDekqWkD |
| Rat | 1A1 | 366 | PQLPYLEAFILEtfRhsSFVPFTIPHSTiRDTSLNGFyIPKghCvFvNQWQVNHDqelWgD |

Fig-2

PRODUCTION OF ANTI-PEPTIDE ANTIBODIES AGAINST CYTOCHROME P450

GRANT REFERENCE

Research in this application was supported in part by a contract from the National Institutes of Health (ES 31002).

TECHNICAL FIELD

The present invention relates to a general method for production of form-specific and/or inhibitory antipeptide antibodies against cytochromes P450 (CYPs). In particular, the present invention produces form-specific, inhibitory antibodies against rat CYP2B1.

BACKGROUND OF THE INVENTION

Cytochromes P450 (CYPs) play an active role in the metabolism of numerous physiological substrates such as steroid hormones, fatty acids, prostaglandins and bile acids, as well as countless xenobiotics, including drugs, chemical carcinogens, insecticides, petroleum products, and other environmental pollutants. Oxidative metabolism catalyzed by CYP can result in detoxification. However, in some instances it results in metabolic activation of a chemical to cytotoxic and/or carcinogenic form. Certain forms of CYP are associated with disease. For example, CYP2E1 is associated with liver disease since treatment with diallyl sulfate which suppresses CYP2E1 prevents liver disease.

Characterization of cytochrome P450, a superfamily of more than 160 known members (Nelson et al., 1993), continues to provide valuable information about protein structure-function relationships and the regulation of gene expressions. The human and rodent genomes contain at least 50 P450 genes which are classified into at least ten families according to amino acid sequence data (Gotoh, 1992).

A nomenclature system for the P450 system has been set forth in Nelson et al. (1993) and will be used herein unless otherwise noted. Briefly, for the gene and cDNA, the italicized root symbol "CYP" for humans and all nonhuman species except mice, representing "cytochrome P450" is used (in mice the root is Cyp). This root is followed by an Arabic number denoting the family, a letter designating the subfamily and an Arabic numeral representing the individual gene within the subfamily. The same nomenclature is also used for the mRNA and protein product of the gene without italicization. Alternative nomenclature is also used either (1) drop the root designation and use only the alphanumeric designation following the root CYP or (2) replace the root with P450.

The term form-specific refers to antibody that is specific for one form, i.e. an enzyme that is coded for by a specific gene within a subfamily. The form-specific antibody appears to be directed to a unique epitope on the enzyme, one that is not found on other forms of CYP. The term inhibitory refers is used to indicate antibody that inhibits the catalytic activity of the enzyme.

The enzymes encoded for by these genes show partial sequence overlap but distinct substrate specificities. Much work has been directed to determining which parts of a P450 protein are involved in recognition and binding of substrates and hence determining substrate specificity (Gotoh, 1992).

CYP2B1 has 97% identity with the primary sequence of CYP2B2 (Guengerich et al., 1982; Waxman and Walsh, 1982; Waxman et al., 1983), but they are products from distinct genes. Only 16 amino acids out of approximately 500 residues are different. However, these 16 amino acid substitutions render 2B1 different from 2B2 with respect to substrate specificity and catalytic rate. CYP2B1 exhibits an approximately 5-fold higher catalytic activity toward benzphetamine (Guengerich et al., 1982) and testosterone (Waxman and Walsh, 1982) than does CYP2B2. Further, 2B1 has an approximately seven-fold greater catalytic activity than 2B2 toward pentoxyresorufin (Lubet et al., 1985). However, 2B2 has a much higher catalytic activity than 2B1 in formation of methylhydroxylidocaine from lidocaine (Oda et al., 1989).

One of the main tools in studies of cytochrome P450 are polyclonal and monoclonal antibodies directed against the CYPs. The similarity in their primary sequences, however, leads to cross-reactivity of polyclonal antibodies to other forms in the same subfamilies even following extensive affinity purification. Furthermore, polyclonal or monoclonal antibodies produced against whole CYP molecules are generally not inhibitory because binding of the antibodies to antigenic sites on CYPs do not necessarily inhibit the catalytic activities of the CYPs.

Antipeptide antibody production against synthetic peptides was determined to be an efficient method for the production of specific antibodies against CYPs (Frey et al., 1985; Edwards et al., 1990; Edwards et al., 1991a and 1991b; Friedberg et al., 1991; Murry et al., 1993). The versatility in the selection of epitopes for antipeptide antibody production facilitated generation of antibodies directed against epitopes involved in catalytic activity of CYPs. In general, antipeptide antibodies so far produced against CYPs are not form-specific nor completely inhibitory toward catalytic activities (Frey et al., 1985; Edwards et al., 1990; Edwards et al., 1991a and 1991b; Friedberg et al., 1991; Murry et al., 1993).

Friedberg et al. (1991) reported that antipeptide antibodies, produced against a recombinant fusion peptide of CYP2B1 or CYP2B2 and a P450 unrelated protein, were neither form-specific nor inhibitory. Usually, antipeptide antibodies produced against recombinant fusion peptides are not inhibitory because these antibodies do not recognize the native peptides (Friedberg, 1991).

It would be useful to have antibodies which are form-specific to identify CYPs which are involved in the metabolism of non-physiological compounds/substances, such as drugs and chemicals or physiological substances. Further, it would be useful to be able to inhibit a specific CYP either to allow the use of a drug which would normally be degraded by the CYP or conversely to prevent the metabolic activation of a chemical to a toxic form.

SUMMARY OF THE INVENTION AND ADVANTAGES

According to the present invention, a method for production of a form-specific and/or inhibitory antibody against a cytochrome P450 protein is disclosed. The method includes the steps of selecting a cytochrome P450 protein against for which a form-specific and/or inhibitory antibody is needed. The amino acid sequence of the selected cytochrome P450 protein is determined and aligned with a comparison amino acid sequence using an alignment algorithm. The comparison sequence has been analyzed utilizing x-ray crystallography and sections of the sequence have been classified as a substrate recognition site. A peptide sequence corresponding to a region of a substrate recognition site is identified and a peptide of the selected sequence prepared. Using the peptide as an immunogen, a form-specific and/or inhibitory antibody is produced. In a model system, the cytochrome P450 protein is selected from the CYP2 family.

The method for production of form-specific and/or inhibitory antibodies against CYPs provides valuable tools for Western blot analyses, enzyme-linked immunosorbent assay (ELISA), purification of CYPs by immunoaffinity chromatography, inhibition studies to identify CYPs involved in metabolism of physiological substances, drugs and other chemicals, and for use as a therapeutic.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1(A–C) illustrates amino acid identity, hydropathy index and predicted secondary structure information of amino acid sequences selected for rat CYP2B1 antipeptide antibody production, FIG. 1A shows alignment of amino acid sequences deduced from rat CYP2B1 cDNA sequences using GENALIGN™ from INTELLIGENETICS™ program with the segment of CYP2B1 amino acid sequence selected for antibody production underlined and capital letters denote conserved amino acid residues, FIG. 1B shows the hydropathic character of the amino acid sequences selected for 2B1 antibody production using the method of Kyte and Doolittle (1982) with windowing average at residue "i" calculated across 6 residues and the symbol "+" or "−" indicating residues with a charged side chain at physiological pH, FIG. 1C shows secondary structure forming propensities of CYP2B1 peptides, the selected sequences are marked in bold type wherein "A", "B" and "T" denote α-helix, β-sheet, and β-turn, respectively;

FIG. 2 shows the amino acid sequences deduced for rat CYP2B1, CYP2B2, CYP1A1, CYP1A2, and CYP101A and are aligned using GENALIGN™ (IntelliGenetics, Inc.), with the sequences against which anti-2B1 IgG was produced shaded, the region corresponding to α-Helix K, and β-Sheets 3 and 4 are labeled and the substrate-binding residues are boxed on a segment of the CYP101A peptide sequence, the substrate recognition site (SRS)-5 of CYP2B2 is underlined, and the SRS-5 of CYP2B1, CYP1A1 and CYP1A2 are assigned and boxed;

DETAILED DESCRIPTION OF THE PREFERRED EMBODIMENT

Figure 3A:
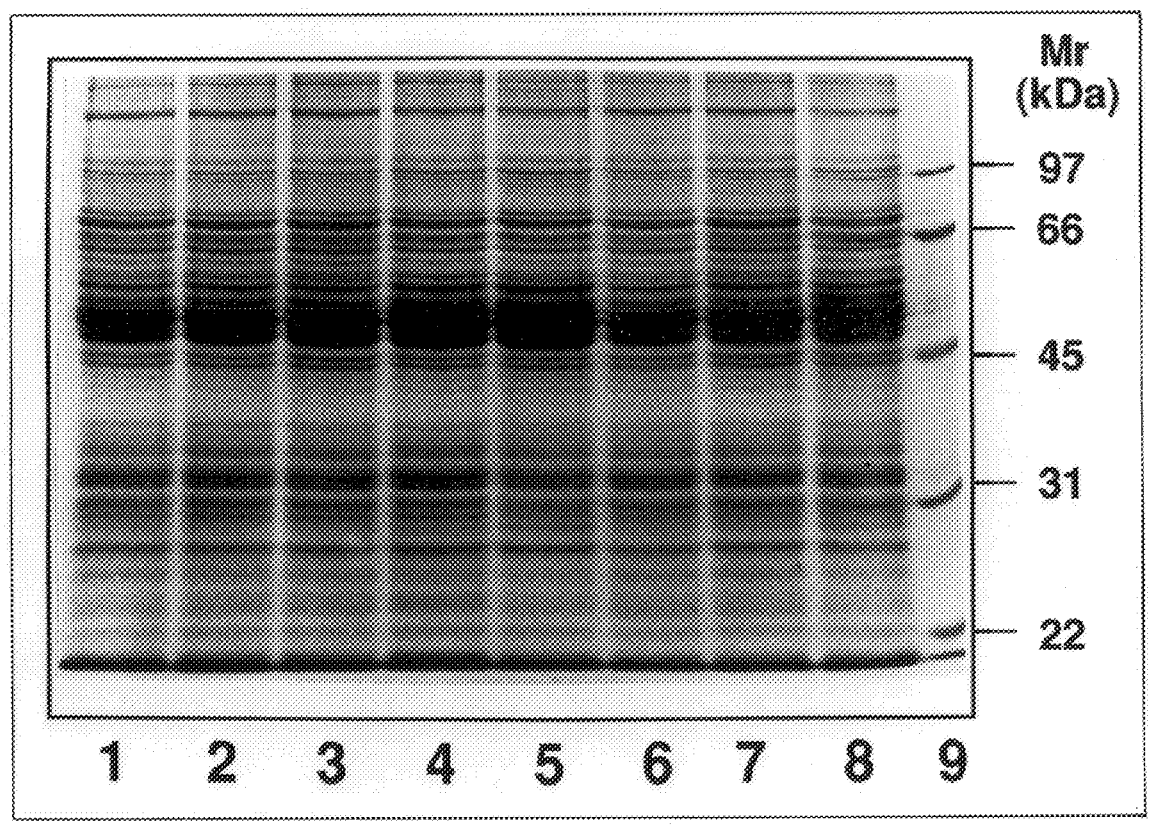
FIG. 3A–C are photographs of SDS-PAGE and Western blot analysis of antipeptide IgG produced against a rat CYP2B1 synthetic peptide fragment using microsomes obtained from rats following treatment with various inducers, (FIG. 3A) SDS-PAGE, (FIG. 3B) Western blot analyses of rat hepatic microsomes using anti-rabbit 2B4 polyclonal antibody and (FIG. 3C) Western blot analyses of rat hepatic microsomes using 2B1 antipeptide IgG, wherein lanes 1 through 8 contained 10 μg of microsomal proteins with lanes 1 and 6, hepatic microsomes obtained after 3 days of corn oil treatment (2 ml/kg/day, i.p.), lanes 2 and 3, hepatic microsomes obtained from untreated rats, lane 4, hepatic microsomes obtained following 3 days of pyridine (PY) treatment (200 mg/kg/day, i.p.), lanes 5, hepatic microsomes obtained following 3 days of phenobarbital (PB) treatment (100 mg/kg/day, i.p.), lane 7, hepatic microsomes obtained following 3 days of clofibrate treatment (200 mg/kg/day, i.p.), lane 8, hepatic microsomes obtained following 3-methylcholanthrene (MC) treatment (25 mg/kg, i.p.), and lane 9, molecular weight markers.

The present invention relates to a general method for production of form-specific and/or inhibitory antipeptide antibodies against a cytochrome P450 (CYP). The method includes the steps of selecting a cytochrome P450 protein against which a form-specific and/or inhibitory antibody is wanted. In a model system the CYP2B subfamily was selected.

The amino acid sequence of the selected cytochrome P450 protein is determined and aligned with an amino acid sequence of a cytochrome enzyme which has been analyzed utilizing x-ray crystallography. The alignment is done using an alignment algorithm.

In a preferred embodiment, the alignment algorithm of Gotoh (1992) is used. The sequence can be determined for the cytochrome P450 protein from the CYP sequence in sequence databases such as GenBank™ or by sequencing cDNA, mRNA or protein of the selected CYP itself.

An amino acid sequence corresponding to a region of a substrate recognition site as defined by Gotoh (1992) is identified and a peptide from the selected sequence is prepared. In the preferred embodiment, a bacterial sequence for P450 is used. The candidate sequences for the peptide are selected from relatively hydrophilic areas of the protein, and by avoiding areas that have a tendency to form α-helical structure. In a preferred embodiment, the amino acid sequence was found and a peptide sequence selected from those regions which corresponds to a Substrate Recognition Site of CYP as proposed by Gotoh (1992) in *Pseudomonas putida* P450 101A (P450cam).

In general, as used herein, the region of the substrate recognition site includes the substrate recognition site itself (as generally defined with x-ray crystallography) and extends approximately at least ten amino acids on either side. The region includes those sequences which when the antibody binds to them inhibits binding at the substrate recognition site.

The peptide can be prepared by synthesizing a peptide based on the sequence, or prepared recombinantly by cloning techniques or the natural gene product and/or portions thereof may be isolated and used. The candidate peptide sequence can include the entire amino acid sequence corresponding the region of the substrate recognition site. Alternatively, the candidate sequence can be smaller than the region of the substrate recognition site. Further, the enzyme (either isolated or recombinant) can be cleaved at the beginning or the end of a substrate recognition site, and the cleaved product containing the SRS region (or portion thereof) at either the carboxyl or amino terminal end can be prepared in the method of the present invention. For example, a fragment which contains the SRS region (or portion thereof), at either the carboxyl- or amino-end, can be prepared by expression of the CYP gene or cDNA.

In one embodiment, the amino acid sequence of the peptide is selected and synthesized based on the amino acid sequence deduced from the 2B1 cDNA sequence in GenBank™, (a) by comparing sequence homology, by selecting peptide sequences from relatively hydrophilic regions of the protein, and by avoiding regions that have a tendency to form a-helical structure, and (b) by selecting a peptide sequence of CYP2B1 which corresponds to Substrate Recognition Site (SRS) 5 of CYP2B1, as proposed by Gotoh (1992), following alignment of the 2B1 amino acid sequence with a Pseudomonas putida P450 101A (P450cam), of which substrate binding sites have been identified by X-ray crystallographic studies (Poulos et al., 1985; Poulos et al., 1987; Poulos, 1991). A region of SRS 5 of CYPs can be identified by aligning amino acid sequence of CYP using the alignment algorithm of Gotoh (1992).

Gotoh proposed six putative Substrate Recognition Sites (SRSs) in mammalian CYPs by aligning amino acid sequences of mammalian P450s with that of bacterial P450 101A, of which substrate binding sites are identified by X-ray crystallographic studies of a substrate-bound enzyme (Poulos et al., 1985; Poulos et al., 1987; Poulos, 1991). The SRS 5, as proposed by Gotoh (1992), was selected for production of the synthetic peptide antigen following alignment of CYP2B1 amino acid sequence with those of P450 101A and CYP2B2 (Mizukami et al., 1983). The SRS 5 regions of mammalian CYPs correspond to β-Sheet 3 of P450 101A (Poulos et al., 1985; Poulos et al., 1987; Poulos, 1991).

A synthetic peptide is then prepared based on the identified sequence utilizing methods for peptide synthesis known in the art or by commercial laboratories specializing in such synthesis. In one embodiment of the invention, the synthetic peptide Val-Pro-Ile-Gly-Val-Pro-His-Arg-Val-Thr-Lys-Asp (amino acids 363–374) (SEQ ID No:1) was selected based on published cDNA sequences (Yuan et al., 1983) for rat CYP2B1.

Using the prepared peptide as an immunogen, a form-specific and/or inhibitory antibody is produced. Antibodies may be either monoclonal or polyclonal. Such peptides can be used to produce antibodies by standard antibody production technology well known to those skilled in the art as described generally in Harlow and Lane, *Antibodies: A Laboratory Manual,* Cold Spring Harbor Laboratory Press, Cold Spring Harbor, N.Y., 1988 or by commercial laboratories specializing in preparing antibodies.

For producing polyclonal antibodies, a host, such as a rabbit or goat, is immunized with the protein or peptide, generally with an adjuvant and, if necessary, coupled to a carrier; antibodies to the protein are collected from the sera.

For producing monoclonal antibodies, the technique involves hyperimmunization of an appropriate donor, generally a mouse, with the protein or peptide fragment, and isolation of splenic antibody producing cells. These cells are then fused to a cell having immortality, such as a myeloma cell, to provide a fused cell hybrid which has immortality and secretes the required antibody. The cells are then cultured in bulk and the monoclonal antibodies harvested from the culture media for use.

The antibody when produced can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice,* Blackwell Scientific Publications, Oxford, 1982.) The binding of antibodies to a solid support substrate is also well known in the art (see for a general discussion Harlow & Lane Antibodies: A Laboratory Manual, Cold Spring Harbor Laboratory Publications, New York, 1988). The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination.

In one embodiment, antipeptide antibodies directed against rat CYP2B1 were produced based on the CYP2B1 amino acid sequence deduced from cDNA sequence (Yuan, 1983) of rat CYP2B1 (accession number of GenBank and EMBL=M37134) (Nelson et al., 1993). The 2B1 antipeptide antibody did not cross-react with CYP2B2 as evidenced by Western blot analysis. The difference between CYP2B1 and CYP2B2 of only two amino acid residues among the 12 amino acid residues in the peptide from the selected region was sufficient to produce an antibody specific to CYP2B1, i.e. a form-specific antibody.

The form-specific anti-CYP2B1 antipeptide antibody, which binds directly to the synthetic 2B1 peptide antigen, also recognizes purified CYP2B1 as well as 2B1 expressed in microsomes obtained from rats following phenobarbital (PB) treatment in a non-denaturing state as evidenced by ELISA. The binding of CYP2B1 antibody to the amino acid sequence selected for 2B1 antibody production, which coincides with one of the Substrate Recognition Sites (SRSs) of mammalian CYPs as proposed by Gotoh (1992) abolishes pentoxyresorufin (PR) O-dealkylase activity of 2B1/2B2 expressed in microsomes obtained from rats following PB treatment as well as inhibits benzphetamine binding to CYP2B1. The inhibition of PR 0-dealkylase activity by anti-CYP2B1 IgG was not a result of non-specific interaction with a cytochrome P450 or NADPH-P450 reductase.

Figure 5:
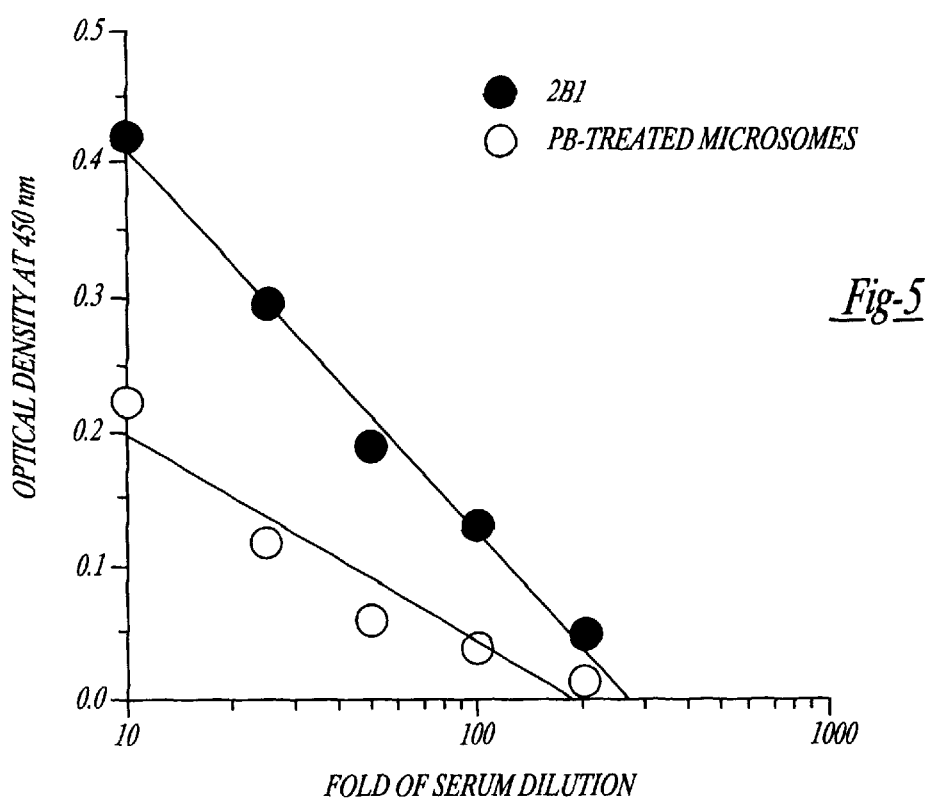
FIG. 5 is a graph of an enzyme linked immunosorbent assay (ELISA) of anti-2B1 antibody using microplates coated with purified 2B1 (●) or rat hepatic microsomes obtained after phenobarbital treatment (○)

A hypothesis for the mechanism of action of the form-specific inhibitory antibodies can be made but it is not to be construed as limiting the present invention to this one mode of action. These results indicate that CYP2B1 antipeptide antibody recognizes the peptide sequence of CYP2B1 selected for antipeptide antibody production in both denaturing (Western blot analysis) and non-denaturing (ELISA and inhibition assays of catalytic activity and substrate binding) conditions. Poulos et al. (1986) reported that analysis of crystal structures of cytochrome P450cam revealed only a minor conformational change as a result of binding campor. The β-sheet 3 of CYP101A, which corresponds to amino acid residues 363–371 of CYP2B1, is located in a substrate binding pocket. The selected sequence (SEQ ID No:1) is in the substrate binding pocket and is therefore expected to be inaccessible to large molecules such as antibodies. It was therefore unexpected to find that the antibody directed against the peptide of SEQ ID No:1 recognized the selected sequence in the substrate binding pocket of CYP2B1 in a non-denaturing condition as evidenced by inhibition of catalytic activity (Table 1) and substrate binding (FIG. 6) of CYP2B1 and by binding to CYP2B1 in an ELISA (FIG. 5).

Hence, antibodies can be made against peptides identified from the substrate binding regions of cytochrome P450 with the present invention. These antibodies will be inhibitory and/or form-specific. The selection of the 2B subfamily shows the validity of the method of the present invention, in that form-specific inhibitory antibodies can be made that distinguish between P450 enzymes with minimal differences in sequences.

The present invention provides antibodies which are both inhibitory and form-specific and can be used not only as analytical tools to identify CYPs which are involved in the metabolism of drugs and physiological substances but also can be used as therapeutics to inhibit a specific CYP (see Symposium, 1992).

The above discussion provides a factual basis for the production and use of form-specific and/or inhibitory antibodies directed against cytochrome P450 proteins. The methods used with and the utility of the present invention can be shown by the following examples.

EXAMPLE

METHODS:

Reagents. Pyridine was purchased from Aldrich Co. (Milwaukee, Wis.). Alkaline phosphatase-conjugated donkey anti-goat Immunoglobulin G (IgG), alkaline phosphatase-conjugated donkey anti-rabbit IgG and horseradish peroxidase (HRP)-conjugated goat anti-rabbit IgG were purchased from Jackson ImmunoResearch Laboratories, Inc. (West Grove, Pa.). Other reagents were purchased from Sigma Chemical Co. (St. Louis, Mo.).

Production of Antipeptide Antibodies. A peptide sequence selected based on cDNA sequences was synthesized by Research Genetics (Huntsville, Ala.) and coupled to a poly-L-lysine core as described previously (Tam, 1988; Posnett et al., 1988). The coupled peptide, referred to as MAP, is then mixed with an equal volume of Freund's adjuvant and subcutaneously injected into a pair of rabbits (White New Zealand rabbit, approximately 3 kg body weight) for each sequence. The total injection volume for a rabbit per immunization is 1 ml (0.5 mg of peptide). Two booster immunizations (0.5 mg each in Freund's incomplete adjuvant) are carried out at 2 and 6 weeks after the first immunization.

The IgG fractions of the antibodies produced against rat CYP2B1 peptide are purified from serum using a protein-G affinity column (Pierce Co., Rockford, Ill.), or by precipitation of contaminating proteins with caprylic acid followed by precipitation of IgG fractions in the supernatant with ammonium sulfate (0.277 g per mL to give 45% saturation) as previously described (Reik et al., 1987).

Production of Polyclonal Antibody against CYP. Antibodies against rabbit CYPs were raised in yellow goats. Each goat was immunized with an initial 100 $\mu$g aliquot of a rabbit CYP emulsified in Freund's complete adjuvant and injected subcutaneously. At two week intervals, the animals were boosted four times with 100 $\mu$g aliquot of the rabbit CYP emulsified with Freund's incomplete adjuvant.

Microsome Preparation. Male Sprague-Dawley rats (160–200 g) were treated with phenobarbital (PB) (100 mg/kg/day, for 3 days, i.p.), pyridine (PY) (200 mg/kg/day, for 3 days, i.p.), 3-methylcholanthrene (MC) (25 mg/kg, single injection, i.p.), corn oil (2 mL/kg/day, for 3 days, i.p.), and clofibrate (200 mg/kg/day, for 3 days, i.p.). Rats were fasted 18 hours prior to sacrifice.

Microsomes were prepared from rat liver as described previously (Kaul and Novak, 1987; Kim et al., 1992; Kim et al., 1993; Kim et al., 1993) and stored at −80° C. in 50 mM Tris acetate buffer, pH 7.4, containing 1 mM EDTA and 20% glycerol until used. Protein was assayed by the method of Bradford (1976) using the Bio-Rad Protein Assay (Bio-Rad, Richmond, Calif.). Total P450 content in microsomal suspensions was determined according to the procedure of Omura and Sato (Omura and Sato, 1964).

Enzyme assays. Previously published procedures were used to monitor pentoxyresorufin (PR) O-dealkylase activity (Lubet et al., 1985) and ethoxyresorufin O-deethylase activity (Burke and Mayer, 1974). Inhibition of pentoxyresorufin (PR) O-dealkylase activity and ethoxyresorufin O-deethylase activity by CYP2B1 antipeptide IgG was assayed using liver microsomes obtained from PB- and 3-MC-treated rats, respectively. Briefly, microsomal protein (1 nmole P450) obtained following three days of treatment with 100 mg PB/kg/day, or a single injection of 25 mg 3-MC/kg, was preincubated with various amounts of anti-2B1 for 5 minutes. The preincubation mixture contained 10 $\mu$M pentoxyresorufin or 10 $\mu$M ethoxyresorufin in 50 mM potassium phosphate buffer, pH 7.4. The enzyme activity assay was initiated by adding 1 mM NADPH to the reaction mixture. The emission of fluorescence produced by resorufin was monitored for 2.5 minutes at 25° C. using an SLM Aminco SPF-500C spectrophotometer. The excitation wavelength was 522 nm and emission wavelength was 586 nm.

Inhibition of Binding Spectra of CYP2B1 with Benzphetamine by Addition of Antipeptide Antibody against CYP2B1. Difference binding spectrum of benzphetamine was carried out with CYP2B1 (0.5 nmol/ml) in 50 mM potassium phosphate buffer, pH 7.4. Inhibition of binding of benzphetamine was carried out with (5, 10 or 15 mg IgG /nmol 2B1) or without antibodies.

Enzyme-linked Immunosorbent Assay (ELISA) of CYP2B1 Antipeptide Antibody. The titer of the rabbit antisera was determined by ELISA using microplates coated with the 2B1 multiple antigenic peptide (MAP) complex (1 $\mu$g/well) or purified 2B1 (0.5 $\mu$g/well), or rat hepatic microsomes (10 $\mu$g/well) obtained after phenobarbital treatment (100 mg/kg/day, for three days, i.p.). The microplates were treated with horseradish peroxidase (HRP)-conjugated goat anti-rabbit IgG as previously described (Sesardic et al., 1986). The bound enzyme conjugate was detected by the addition of 3,3'5,5'-tetra-methylbenzidine (TMB). For a more intense signal, the plates were stopped with an acid stop solution and read at 450 nm.

Electrophoresis and Western Blot Analysis. SDS-PAGE was carried out on 10% mini-gels using a Bio-Rad Mini-Protein II system (Bio-Rad Laboratories, Hercules, Calif.) according to the procedure of Laemmli (1970). The following molecular weight standards were used in SDS-PAGE gels: a mixture of rabbit phosphorylase B, 97 kDa; bovine serum albumin, 66 kDa; Ovalbumin, 45 kDa; bovine carbonic anhydrase, 31 kDa; and soybean trypsin inhibitor, 22 kDa (Bio-Rad Laboratories).

Western blot analyses were carried out as previously described (Kim et al., 1992). Briefly, hepatic microsomes (10 $\mu$g) were separated by SDS-PAGE and transferred to a nitrocellulose membrane. The membrane was treated with a primary antibody followed by incubation with alkaline phosphatase-conjugated donkey anti-rabbit or anti-goat IgG as the secondary antibody. Bands were visualized by incubating the membrane with a mixture of nitroblue tetrazolium and 5-bromo-4-chloro-3-indolyl-phosphate in Tris buffer solution.

Sequence Analysis and Alignment of Cytochromes P450. The cDNA sequences (Yuan et al., 1983; Mizukami et al., 1983) of rat CYP2B1 (accession number of GenBank and EMBL=M37134) (Nelson et al., 1993) and CYP2B2 (accession number of GenBank and EMBL=J00720 to J00728) (Nelson, 1993), CDNA sequences (Yabusaki et al., 1984; Kawajiri et al., 1984) of rat CYP1A1 (accession number of GenBank and EMBL=X00469) (Nelson, 1993) and CYP1A2 (accession number of GenBank and EMBL= K02422) (Nelson, 1993), and CDNA sequence (Unger et al., 1986) of P. putida CYP101A1 (accession number of GenBank and EMBL=M12546) (Nelson, 1993) were obtained from GENBANK™, edited to obtain in-frame coding sequences, and translated into amino acid sequences using the FINDSEQ™, GENED™ and SEQ™ routines, respectively, of the INTELLIGENETICS™ (IG) program (IntelliGenetics, Inc., Mountain View, Calif.).

Protein sequences of cytochromes P450 were aligned using GENALIGN™ of the IG program. The hydrophobicity of the CYP2B1 amino acid residues was determined using the PEP™ routine of the IG program by the method of Kyte and Doolittle (1982) with a window size of 6 amino acid residues. The tendency of the selected CYP2B1 peptide to form secondary structure was predicted using the PEP™ routine of the IG program by the method of Chou and Fasman (1974).

RESULT

Antipeptide antibodies directed against rat CYP2B1 were produced based on the CYP2B1 amino acid sequence deduced from cDNA sequence (Yuan et al., 1983) of rat CYP2B1 (accession number of GenBank and EMBL= M37134) (Nelson et al., 1993). The hydrophobicity of CYP2B1 amino acid residues was determined using the method of Kyte and Doolittle Kyte and Doolittle, 1982). The selected peptide sequences for CYP2B1 antibody production was located in a relatively hydrophilic region (FIG. 1). The tendency of the selected CYP2B1 peptides to form secondary structure was predicted using the method of Chou and Fasman (1974). The tendency to form a-helix was predicted to be very low for the peptides selected for CYP2B1 antibody production (FIG. 1).

The CYP2B1 amino acid sequence was aligned with those of CYP101A1 (P450 cam) and CYP2B2 and the amino acid sequence selected for production of an antipeptide antibody against CYP2B1 was found to be one of the Substrate Recognition Sites (SRSs) proposed by Gotoh (1992, FIG. 2).

Figure 3B:
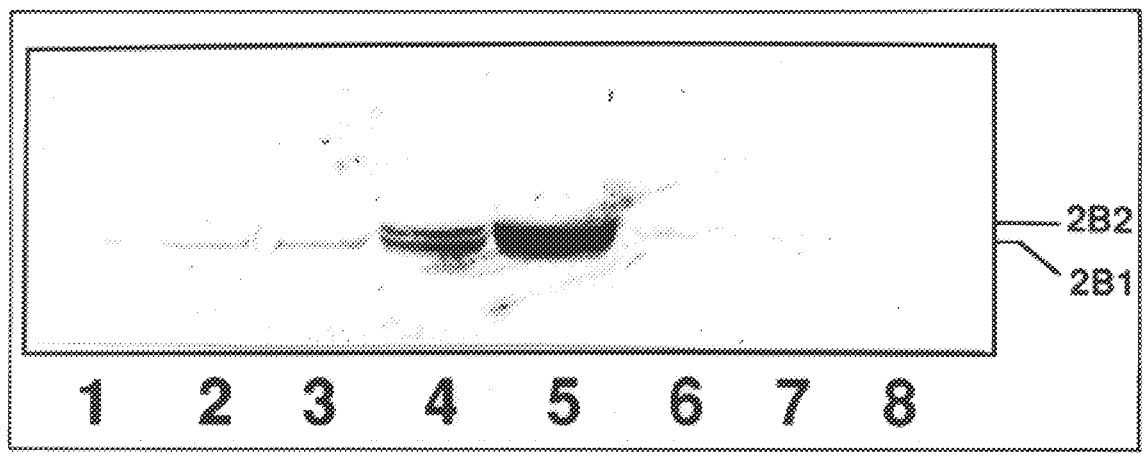
Figure 3C:
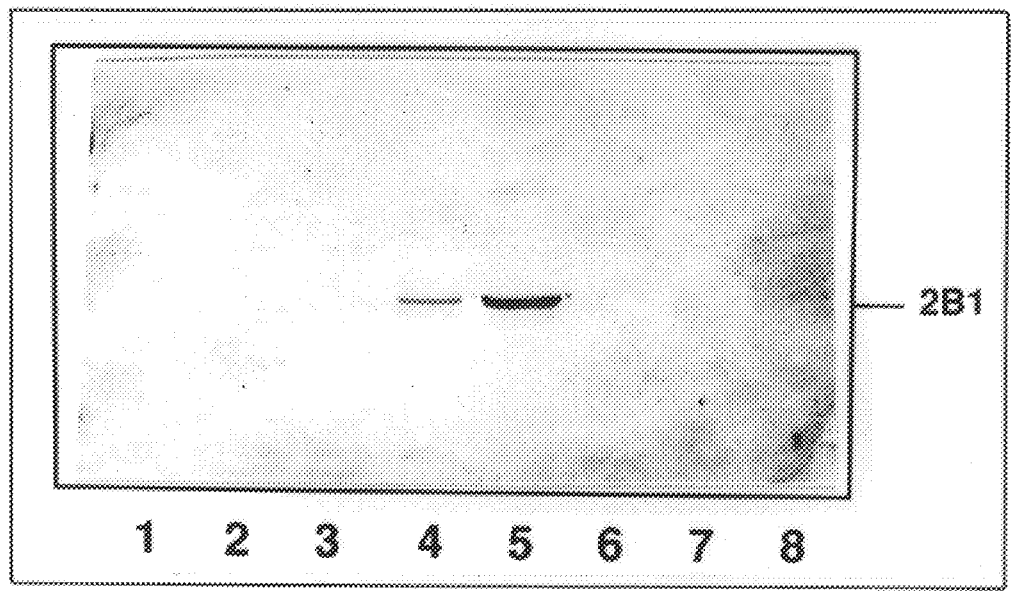

The anti-CYP2B1 antibody recognized CYP2B1 but did not cross-react with CYP2B2 expressed in microsomes obtained from rats following PY or PB treatment (FIG. 3).

Figure 4:
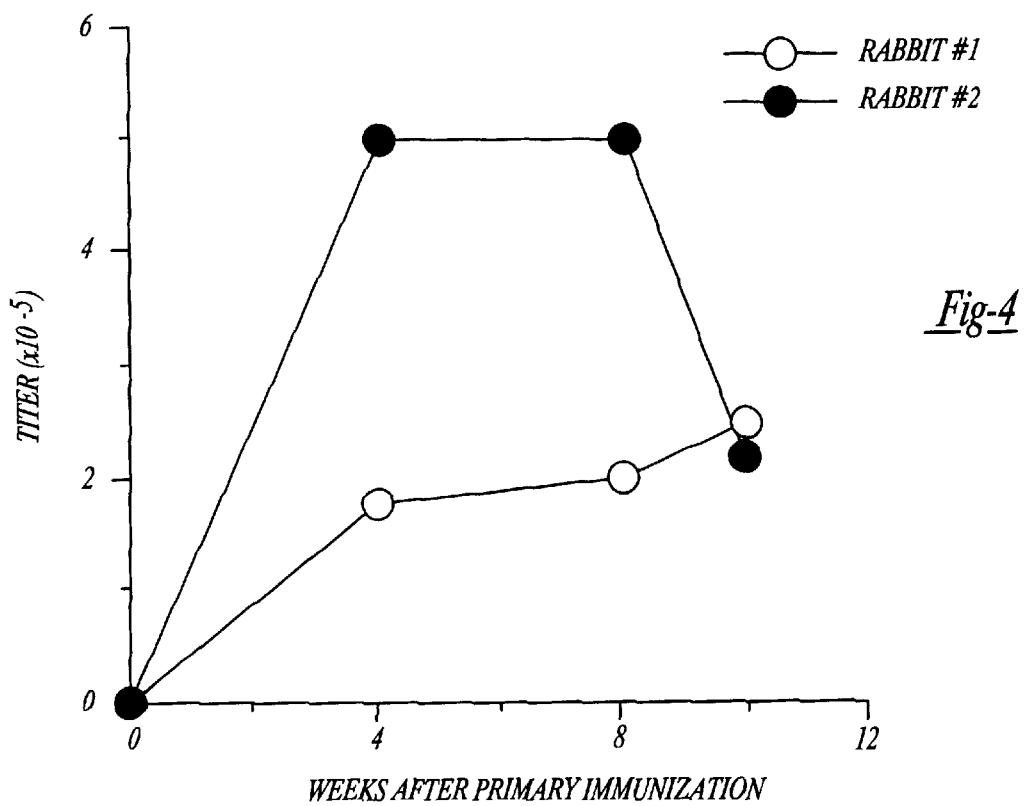
FIG. 4 is a graph of the reciprocal of the serum dilution (titer) following immunization with the synthetic peptide from 2B1, determined in an enzyme-linked immunosorbent assay (ELISA) using microplates coated with CYP2B1 multiple antigenic peptide (MAP)

The titer of the rabbit antisera increased following immunization as evidenced by enzyme-linked immunosorbent assay (ELISA) using microplates coated with CYP2B1 MAP complex (FIG. 4). The anti-CYP2B1 antibody recognized purified CYP2B1 and microsomes obtained following phenobarbital treatment in non-denaturing conditions as evidenced by ELISA (FIG. 5).

Figure 6A:
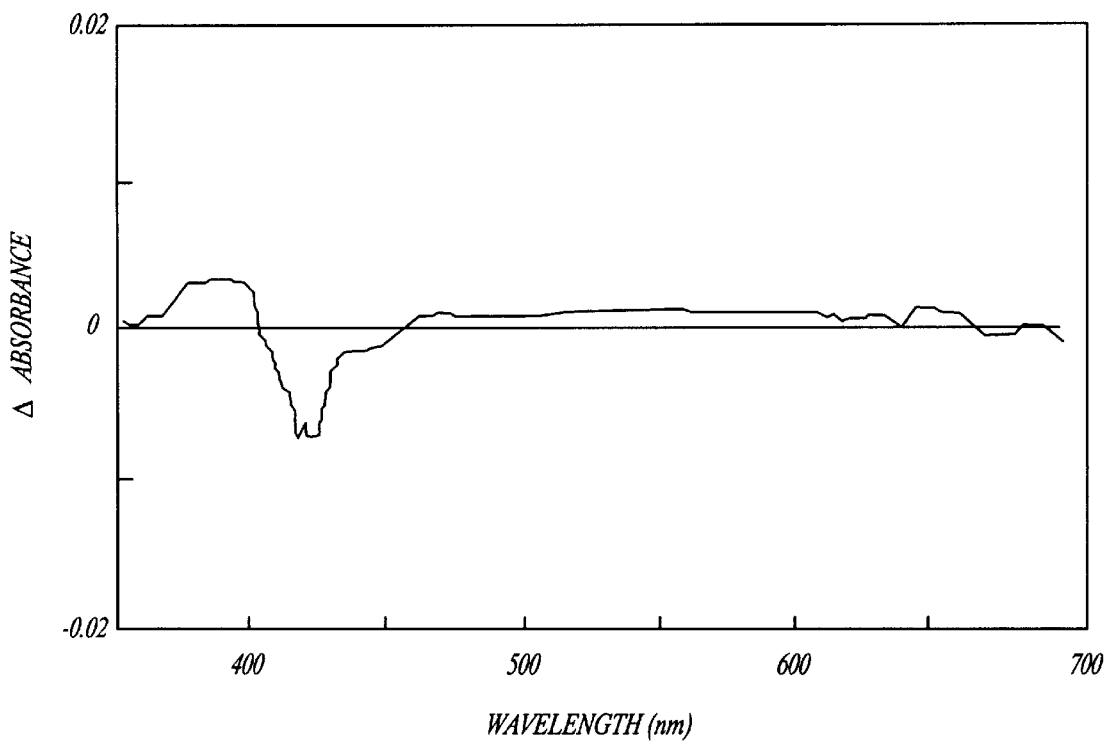
FIG. 6A–B is a difference binding spectra of CYP2B1 with benzphetamine (FIG. 6A) without addition of antipeptide antibody against CYP2B1 and (FIG. 6B) with the antipeptide antibody against CYP2B1.
Figure 6B:
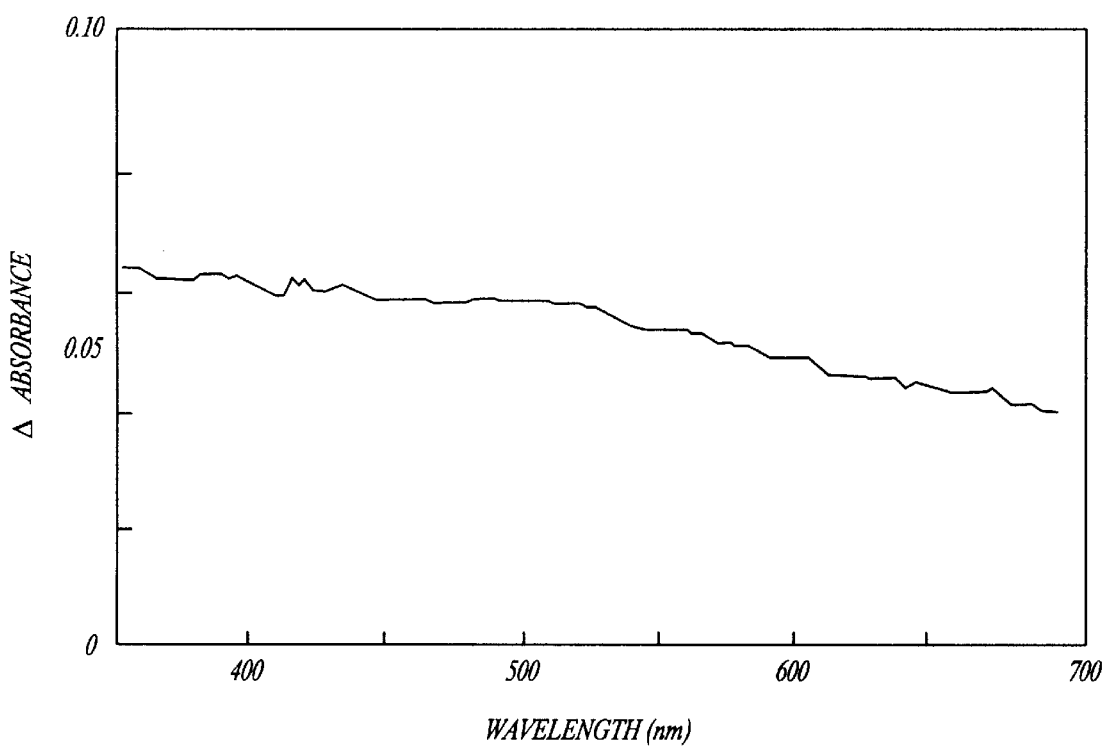

The anti-CYP2B1 IgG abolished Type I binding spectra of CYP2B1 produced by benzphetamine at the ratio of 15 mg IgG to nmol P450 (FIG. 6). At the ratio of 5 and 10 mg IgG to nmol P450, the binding of bezphetamine to CYP2B1 was inhibited 14% and 50%, respectively. These results showed that the antibody inhibits binding of CYP2B1 to its substrate.

The 2B1 anti-peptide antibody inhibited pentoxyresorufin (PR) O-dealkylase activity of microsomes from phenobarbital (PB)-treated rats in a dose-dependent manner but did not inhibit ethoxyresorufin (ER) O-deethylase activity of microsomes obtained from 3-methylcholanthrene (MC)-treated rats (Table 1), showing that the inhibition of PR O-dealkylase activity by anti-CYP2B1 IgG was not a result of non-specific interaction between anti-CYP2B1 and a cytochrome P450 or between anti-CYP2B1 and NADPH-P450 reductase.

Throughout this application various publications are referenced. Full citations for the referenced publications not included herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

| Antipeptide Antibody | Pentoxyresorufin O-Dealkylase Activity of Liver Microsomes Obtained from PB-treated Rats | Ethoxyresorufin O-Deethylase Activity of Liver Microsomes Obtained from 3-MC-treated Rats |
|---|---|---|
| | mg IgG/nmol P450 | % of Control Activity |
| None | 0 | 100 | 100 |
| Anti-2B1 | 1.0 | 95 | NT[a] |
| | 2.5 | 79 | NT |
| | 5.0 | 46 | NT |
| | 7.5 | 34 | NT |
| | 10.0 | 0 | 100 |

[a]Not Tested

REFERENCE

Bradford (1976) "Rapid and Sensitive Method for Quantitation of Microgram Quantities of Protein Utilizing the Principle of Protein-Dye Binding", Anal. Biochem. 72:248–254

Burke and Mayer (1974) "Ethoxyresorufin: Direct Fluorimetric Assay of Microsomal O-Dealkylation which is Preferentially Inducible by 3-Methylcholanthrene", Drug Metab. Dispos. 2(6):583–588

Chou and Fasman (1974) "Prediction of Protein Conformation", Biochemistry 13(2):222–244

Edwards et al. (1990) "An anti-peptide antibody targeted to a specific region of rat cytochrome P-450IA2 inhibits enzyme activity", Biochem. J. 266:497–504

Edwards et al. (1991a) "Antipeptide antibodies in studies of cytochromes P451IA" in Methods in Enzymol. 206:220–233 (Academic Press, N.Y.)

Edwards et al. (1991b) "Identification of a functionally conserved surface region of rat cytochromes P450IA", Biochem. J. (Sept) 280:749–757

Frey et al. (1985) "The structure of phenobarbital-inducible rat liver cytochrome P-450 isoenzyme PB-4", "Production and characterization of site-specific antibodies", J. Biol. Chem. 260:15253–15265

Friedberg et al. (1991) "Production of Site-Specific P450 Antibodies Using Recombinant Fusion Proteins as Antigens", in Methods in Enzymol. 209:193–201 (Academic Press, N.Y.)

Gotoh (1992) "Substrate Recognition Sites in Cytochrome P450 Family 2 (CYP2) Proteins Inferred from Comparative Analyses of Amino Acid and Coding Nucleotide Sequences", *J. Biol. Chem.* 267:83–89

Guengerich et al. (1982) "Purification and characterization of liver microsomal cytochromes P-450: Electrophoretic, spectral, catalytic, and immunochemical properties and inducibility of eight isozymes isolated from rat treated with phenobarbital or β-naphthoflavone", Biochemistry 21:6019–6030

Kaul and Novak (1987) "Inhibition and Induction of Rabbit Liver Microsomal Cytochrome P-450 by Pyridine", *J. Pharmacol. Exp. Ther.* 243:384–390

Kawajiri et al. (1984) "Coding nucleotide sequence of 3-methylcholanthrene inducible cytochrome P-450d CDNA from rat liver", *Proc. Natl. Acad. Sci. U.S.A.*, 81:1649–1653

Kim et al. (1992) "Evidence for Elevation of Cytochrome P4502E1 (alcohol-inducible form) mRNA Levels in Rat Kidney Following Pyridine Administration", *Biochem. Biophys. Res. Commun.* 186:846–853

Kim et al. (1993) "Enhanced Expression of Rat Hepatic CYP2B1/2B2 and 2E1 by Pyridine: Differential Induction Kinetics and Molecular Basis of Expression" 267:927–936

Kyte and Doolittle (1982) "Simple Method for Displaying Hydropathic Character of a Protein", *J. Mol. Biol.*, 157:105–132

Laemmli (1970) "Cleavage of Structural Proteins during the Assembly of Head of Bacteriophage T4", *Nature* (August) 227:680–685

Lubet et al. (1985) "Dealkylation of Pentoxyresorufin: A Rapid and Sensitive Assay for Measuring Induction of Cytochrome(s) P-450 by Phenobarbital and Other Xenobiotics in Rat", *Archiv. Biochem. Biophys.* (April) 238(1):43–48

Mizukami et al. "Gene structure of phenobarbital-inducible cytochrome P-450 in rat liver", *Proc. Natl. Acad. Sci. U.S.A.*, 80:3958–3962

Murry et al. (1993) "Human hepatic CYP1A1 and CYP1A2 content, determined with specific anti-peptide antibodies, correlates with the mutagenic activation of PhIP", *Carcinogenesis* 14:585–592

Nelson et al. (1993) "The P450 Superfamily: Update on New Sequences, Gene Mapping, Accession Numbers, Early Trivial Names of Enzymes, and Nomenclature", *DNA and Cell Biol.* 12(1):1–51

Oda et al. (1989) "Metabolism of Lidocaine by Purified Rat Liver Microsomal Cytochrome P-450 Isozymes", *Biochem. Pharmacol.* 38:4439–

Omura and Sato (1964) "Carbon Monoxide-binding Pigment of Liver Microsomes", *J. Biol. Chem.* 239:2379–2385

Posnett et al. (1988) "A Novel Method for Producing Anti-peptide Antibodies", *J. Biol. Chem.* 263(4):1719–1725

Poulos (1991) "Modeling of Mammalian P450s on basis of P450$_{cam}$ X-Ray Structure", in *Methods in Enzymol.* 206:11–30 (Academic Press, N.Y.)

Poulos et al. (1985) "The 2.6-Angstrom crystal structure of *Pseudomonas putida* cytochrome P-450", *J. Biol. Chem.* 260:16122–16130

Poulos et al. (1987) "High-resolution crystal structure of cytochrome P-450$_{cam}$", *J. Mol. Biol.* 195:687–700

Reik et al. (1987) "A simple, non-chromatographic purification procedure for monoclonal antibodies", *J. Immunol. Methods* 100:123–130

Sesardic et al. (1986) "Inter-relatedness of some isoenymes of cytochrome P-450 from rat, rabbit and human, determined with monoclonal antibodies", *Biochem. J.* 236:569–577

Symposium: Antibody-based Therapeutics for Cancer and Autoimmune Disease, FASEB Meeting, Apr. 5–9, 1992, Anaheim, Calif.

Tam (1988) "Synthetic peptide vaccine design: Synthesis and properties of a high-density multiple antigenic peptide system", *Proc. Natl. Acad. Sci. U.S.A.*, 85:5409–5413

Unger et al. (1986) "Nucleotide sequence of the *Pseudomonas putida* cytochrome P-450$_{cam}$ gene and its expression in *Escherichia coli*", *J. Biol. Chem.* 261:1158–1163

Waxman and Walsh (1982) "Phenobarbital-induced rat liver cytochrome P-450: Purification and characterization of two closely related isozymic forms", *J. Biol. Chem.* 257:10446–10457

Waxman et al. (1983) "Regioselectivity and stereoselectivity of androgen hydroxylations catalyzed by cytochrome P-450 isozymes purified from phenobarbital-induced rat liver", *J. Biol. Chem.* 258:11937–11947

Yabusaki et al. (1984) "Nucleotide sequence of a full-length cDNA coding for 3-methylcholanthrene-induced rat liver cytochrome P-450MC", *Nucleic Acids Res.* 12:2929–2938

Yuan et al. (1983) "Identification and localization of amino acid substitutions between two phenobarbital-inducible rat hepatic microsomal cytochromes P-450 by microsequence analyses" *Proc. Natl. Acad. Sci. USA*, 80:1169–1173

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Val  Pro  Ile  Gly  Val  Pro  His  Arg  Val  Thr  Lys  Asp
 1             5                        10
```

We claim:

1. A method for production of a form-specific and inhibitory antibody against a cytochrome P450 including the steps of selecting a cytochrome P450 protein from the CYP2 family, determining the amino acid sequence of the selected cytochrome P450 protein, aligning the amino acid sequence of the selected cytochrome P450 protein with comparison amino acid sequence using an alignment algorithm to identify a substrate recognition site wherein said comparison amino acid sequence is a cytochrome P450 sequence that has been analyzed utilizing x-ray crystallography or NMR and domains of the sequence are a substrate recognition site, selecting a peptide sequence corresponding to a region of the substrate recognition site, preparing a peptide of the selected sequence, and using the peptide as an immunogen whereby a form-specific inhibitory antibody is produced.

2. The method of claim 1 wherein the substrate recognition site is substrate recognition site 5.

3. The method of claim 2 wherein the selected sequence is Val-Pro-Ile-Gly-Val-Pro -His-Arg-Val-Thr-Lys-Asp (SEQ ID No:1).

4. The method of claim 1 wherein the comparison amino acid sequence is bacterial P450101A.

5. The method of claim 1 wherein the antibody is selected from the group consisting of polyclonal and monoclonal antibody.

6. A method for production of a form-specific antibody against a cytochrome P450 including the steps of selecting a cytochrome P450 protein from the CYP2 family, determining the amino acid sequence of the selected cytochrome P450 protein, aligning the amino acid sequence of the selected cytochrome P450 protein with a comparison amino acid sequence using an alignment algorithm wherein said comparison amino acid sequence is a sequence that has been analyzed utilizing x-ray crystallography or NMR and domains of the sequence are a substrate recognition site, selecting a peptide sequence corresponding to a region of a substrate recognition site, preparing a peptide of the selected sequence, and using the peptide as an immunogen whereby a form-specific antibody is produced.

7. The method of claim 6 wherein the substrate recognition site is substrate recognition site 5.

8. The method of claim 7 wherein the selected sequence is Val-Pro-Ile-Gly-Val-Pro -His-Arg-Val-Thr-Lys-Asp (SEQ ID No:1).

9. The method of claim 6 wherein the comparison amino acid sequence is bacterial P450101A.

10. The method of claim 6 wherein the antibody is selected from the group consisting of polyclonal and monoclonal antibody.

11. A method for production of an inhibitory antibody against a cytochrome P450 including the steps of selecting a cytochrome P450 protein from the CYP2 family, determining the amino acid sequence of the selected cytochrome P450 protein, aligning the amino acid sequence of the selected cytochrome P450 protein with a comparison amino acid sequence using an alignment algorithm wherein said comparison amino acid sequence is a sequence that has been analyzed utilizing x-ray crystallography or NMR and domains of the sequence are a substrate recognition site, selecting a peptide sequence corresponding to a region of a substrate recognition site, preparing a peptide of the selected sequence, and using the peptide as an immunogen whereby an inhibitory antibody is produced.

12. The method of claim 11 wherein the substrate recognition site is substrate recognition site 5.

13. The method of claim 11 wherein the selected sequence is Val-Pro-Ile-Gly-Val-Pro -His-Arg-Val-Thr-Lys-Asp (SEQ ID No:1).

14. The method of claim 11 wherein the comparison amino acid sequence is bacterial P450101A.

15. The method of claim 11 wherein the antibody is selected from the group consisting of polyclonal and monoclonal antibody.

16. A method for production of an antibody against a cytochrome P450, selected from a group consisting of form-specific, inhibitory and form-specific inhibitory antibodies, including the steps of selecting a cytochrome P450 protein, determining the amino acid sequence of the selected cytochrome P450 protein, aligning the amino acid sequence of the selected cytochrome P450 protein with a comparison amino acid sequence using an alignment algorithm wherein said comparison amino acid sequence is a sequence that has been analyzed utilizing crystallography or NMR and domains of the sequence are a substrate recognition site, selecting a peptide sequence corresponding to a region of a substrate recognition site, preparing a peptide of the selected sequence, and using the peptide as an immunogen whereby an antibody selected from the group consisting of form-specific, inhibitory and form-specific inhibitory antibodies is produced.

17. The method of claim 16 wherein the comparison amino acid sequence is a bacterial P450 amino acid sequence.

18. The method of claim 16 wherein the comparison amino acid sequence is bacterial P450101A.

19. The method of claim 16 wherein the antibody is selected from the group consisting of polyclonal and monoclonal antibody.

20. An antibody against a peptide of the amino acid sequence Val-Pro-Ile-Gly-Val-Pro-His-Arg-Val-Thr-Lys-Asp (SEQ ID No:1).

21. An antibody as set forth in claim 20 wherein the antibody is selected from the group consisting of polyclonal and monoclonal antibody.

22. An antibody that is a form-specific inhibitory antibody against a cytochrome P450 protein prepared as set forth in claim 16.

23. An antibody that is a form-specific antibody against a cytochrome P450 protein prepared as set forth in claim 16.

24. An antibody that is an inhibitory antibody against a cytochrome P450 protein prepared as set forth in claim 16.

* * * * *